US 6,598,486 B2
Jul. 29, 2003

(54) PORTABLE DEVICE FOR TESTING THE SHEAR RESPONSE OF A MATERIAL IN RESPONSE TO A REPETITIVE APPLIED FORCE

(75) Inventors: Kent Vilendrer, Eden Prarie, MN (US); Troy Nickel, St. Louis Park, MN (US)

(73) Assignee: EnduraTec Systems Corporation, Minnetonka, MN (US)

( * ) Notice: Subject to any disclaimer, the term of this patent is extended or adjusted under 35 U.S.C. 154(b) by 0 days.

(21) Appl. No.: 09/862,054

(22) Filed: May 21, 2001

(65) Prior Publication Data

US 2002/0170361 A1 Nov. 21, 2002

(51) Int. Cl.[7] .................................................. G01N 3/24
(52) U.S. Cl. .......................................... 73/841; 73/846
(58) Field of Search ........................ 73/849, 841, 846, 73/853

(56) References Cited

U.S. PATENT DOCUMENTS

| | | | | |
|---|---|---|---|---|
| 3,035,437 A | * | 5/1962 | Watkins et al. | 138/31 |
| 3,406,567 A | | 10/1968 | Terry | 73/101 |
| 3,566,681 A | | 3/1971 | Iosipescu et al. | 73/101 |
| 3,854,328 A | | 12/1974 | Schmidt | 73/91 |
| 3,975,950 A | | 8/1976 | Erdei | 73/94 |
| 4,445,387 A | | 5/1984 | Hall et al. | 73/845 |
| 4,854,175 A | * | 8/1989 | Budhu | 73/841 |
| 4,916,954 A | | 4/1990 | Buzzard | 73/799 |
| 5,036,709 A | * | 8/1991 | McRae | 73/841 |
| 5,245,876 A | | 9/1993 | Jones | 73/579 |
| 5,280,730 A | | 1/1994 | Peres et al. | 73/846 |
| 5,289,723 A | | 3/1994 | Thompson et al. | 73/842 |
| 5,461,928 A | * | 10/1995 | Azzolini et al. | 100/258 R |
| 5,585,570 A | * | 12/1996 | Raymond | 73/851 |
| 5,712,431 A | * | 1/1998 | Vilendrer | 73/841 |

* cited by examiner

Primary Examiner—Hezron Williams
Assistant Examiner—Lilybett Martir
(74) Attorney, Agent, or Firm—Nikolai & Mersereau, P.A.; C. G. Mersereau

(57) ABSTRACT

A portable device for measuring the shear properties of a material specimen under applied dynamic circumferential forces against the specimen perpendicular to a longitudinal axis of said specimen. The device may further apply a dynamic force against an end of the specimen. The device includes clamps that hold the specimen at its proximal and distal end, wherein the circumferential force applied to the specimen is affectively applied between the two clamps. The temperature of the specimen may be held constant by controlling the temperature within an environmental chamber through the use of a closed loop PID control system. The force against the specimen is dynamically loaded by a dynamic load reaction frame consisting of a shear load actuator and load reaction structure. A microprocessor-based controller operates the dynamic load reaction frame under closed loop control. The microprocessor-based controller may be servo controlled, utilizing feedback from either a load transducer or either or both of two linear displacement transducers.

15 Claims, 11 Drawing Sheets

US 6,598,486 B2

PORTABLE DEVICE FOR TESTING THE SHEAR RESPONSE OF A MATERIAL IN RESPONSE TO A REPETITIVE APPLIED FORCE

FIELD OF THE INVENTION

This invention relates generally to devices used to test the shear response of a material, and more particularly relates to a portable apparatus and method for testing the viscoelastic response of a material specimen to an applied shear force under either monotonic or dynamic loading conditions. The device of the present invention may apply a circumferential force against the specimen perpendicular to a longitudinal axis of the specimen and may also apply a compression force against an end of the specimen.

BACKGROUND OF THE INVENTION

Over the years, the Federal Highway Administration (FHWA) has been encouraging a modeling technique known as the SuperPave Asphalt Mix Design Model (hereinafter referred to as "superpave") as a method of predicting the life expectancy of various paving mixes. Paving mixes are typically custom tailored to the unique requirements dictated by local traffic, climate, materials selection, and structural section at the pavement site. The superpave model is intended as a useful tool to help estimate the pavement's future long term performance in terms of its resistance to permanent deformation (rutting), fatigue cracking and low temperature cracking.

The superpave modeling technique requires the input of mechanical properties associated with the particular asphalt mix to be modeled. In order to determine the required input properties of the asphalt mix, several tests are performed to determine the linear and non-linear elastic response, viscous behavior, and tertiary creep tendencies of the asphalt mix sample. These tests are characterized by the application of dynamic and monotonic loads or strains in shear and thereafter measuring the resulting strain or stress response. The resulting test data is then implemented in the superpave modeling technique to estimate the life expectancy of the sample.

In order to most effectively estimate the life expectancy of a sample using the superpave technique, the test data should be obtained at the field level. Hence, a portable testing apparatus is desirable to perform the required tests on the sample in the field. To further increase the efficiency of obtaining the required test data, the sample material should not require substantial specimen preparation.

Often times, the sample test data is obtained in a laboratory setting using cumbersome testing equipment known in art as a Superpave Shear Tester (hereinafter the "SST"). The SST includes a fixture that directs a shear load to a cylindrical specimen parallel with the ends of the specimen contained within the fixture. Proper use of the SST requires that the ends of a cylindrical specimen be cut square relative to each other and then glued to metal platens in a precision gluing jig prior to installation in the fixture. The "glued specimen" approach of the SST requires additional time and experience to properly glue and align the specimen. Further, in order to keep the ends of the specimen parallel, precise bearings are required to guide the specimen face as the shear load is applied. The use of bearings creates the possibility of backlash and misalignment. Hence, a need exists for a simple, easy to use, portable device for testing the shear strength of a material in response to an applied force.

Various fixtures have been developed that direct a shear load to a specimen contained within a fixture. In this regard, reference is made to the disclosures of Iosipescu et al., U.S. Pat. No. 3,566,681, Jones, U.S. Pat. No. 5,245,876, Terry, U.S. Pat. No. 3,406,567, Hall et al. U.S. Pat. No. 4,445,387, Peres et al., U.S. Pat. No. 5,280,730, Thompson et al., U.S. Pat. No. 5,289,723, and Buzzard, U.S. Pat. No. 4,916,954. These disclosures generally describe fixtures for applying shear loads to a specimen, but do not describe a fixture suitable for applying a circumferential force against a specimen perpendicular to a longitudinal axis of the specimen.

Iosipescu in U.S. Pat. No. 3,566,681 describes a method and apparatus for shear testing of rocks and other building materials. A rectangular block specimen is described, wherein a v-groove is formed in a middle, top and bottom portion of the block and channels, aligned with the grooves, are formed in the front and back of the block. The fixture described by Iosipescu applies a shear stress proximate the center of the v-groove and channel. A cylindrical specimen held in the fixture described by Iosipescu would tend to rotate within the fixture as the shear force is applied. Further, the clamping of the rectangular specimen by the fixture does not provide for through-zero loading. Also, the fixture described by Iosipescu does not use flexures for maintaining the distance between the two clamping assemblies.

Jones in U.S. Pat. No. 5,245,875 describes a fixture whereby a shear stress is applied to specimen with rectangular beam geometry. Jones describes using the fixture to shear polymeric materials and does not describe an active split clamping system to provide through zero loading and to prevent the specimen from rotating within the fixture. Further, Jones does not describe a fixture that includes flexures for maintaining the distance between the two specimen attachments and there is no mention of measuring specimen strain.

McRae in U.S. Pat. No. 5,911,164 discloses a compaction and pavement design testing machine and method for testing flexible pavement materials. The device described by McRae provides a rotational or gyratory shear testing. The compacting device described by McRae is not simple and portable and further does not apply a force that is perpendicular to the longitudinal axis of the specimen.

Vilendrer in U.S. Pat. No. 5,712,431, describes a device for testing the shear response of a material in response to an applied force. The '431 patent describes applying a shearing force to a cylindrical specimen along the longitudinal axis of the specimen. The specimen could potentially rotate within the fixture as the shear force is applied to the specimen. In contrast to the device described in the '431 patent, the device of the present invention applies a circumferential force against the specimen perpendicular to a longitudinal axis of the specimen, which may be in combination with a compression force against the ends of the specimen.

Thus, there is a need for a device, used for testing a response of a material specimen to shear forces applied to the material specimen, that applies the shear force against the specimen perpendicular to a longitudinal axis of the specimen, that may also apply a compression force against an end of the specimen, and which inhibits twisting or rotation of the specimen as the shear force is applied. The present invention meets these and other needs that will become apparent from a review of the description of the present invention.

SUMMARY OF THE INVENTION

The purpose of the present invention is to provide a portable field shear tester for determining shear stress test data corresponding to various asphalt mixes that can subsequently be used in modeling methods to estimate the future pavement life. The present invention provides a shear tester, wherein the shear strengths of the specimen can be tested with minimal preparation at the field site and with great speed. Testing of the asphalt material is performed by obtaining a cylindrical sample and placing it into a shear fixture that can be subjected to monotonic or dynamic forces, including a circumferential force against the specimen perpendicular to a longitudinal axis of the specimen. The specimen may also be subjected to an additional compression force against an end of the specimen.

The shear-testing device of the present invention includes a base, first and second clamps, and corresponding flexures. The first clamp is attached to the base and clamps about a perimeter of the specimen in proximity to a distal end of the specimen. The second clamp is attached to the first clamp via flexures and clamps about the perimeter of the specimen in proximity to a proximal end of the specimen. The clamps fasten about the perimeter of the specimen with enough force to inhibit rotation of the specimen within the clamps. Without limitation, in the preferred embodiment opposite halves of each clamp are forced together with hydraulics. The flexures have a proximal and distal end, wherein the proximal end of the flexures is attached to the second clamp at the proximal end of specimen, and the distal end of the flexures is attached to the first clamp at the distal end of the specimen. A downward force to the second clamp causes the proximal end of the flexures and the second clamp to move downward while the first clamp remains stationary, thereby applying a circumferential force against the specimen perpendicular to a longitudinal axis of the specimen.

An additional actuator may be coupled to the first clamp to thereby apply a compression force against an end of the specimen. Front and back plates are affixed to the first and second clamps, whereby the plates engage the respective ends of the specimen. The additional actuator applies a force against the plate engaged with the distal end of the specimen. In order to measure the relative displacement between the first and second clamps, when the circumferential or compression force is applied to the specimen, linear displacement transducers may be utilized to measure the same.

The shear fixture is coupled to a monitoring and control system that includes a microprocessor-based servo-controller, which controls, via closed loop feedback, the amplitude and frequency of the applied load or displacement to the shear fixture. A microprocessor-based temperature controller is also used to control the environmental control system temperature.

Those skilled in the art will appreciate that, although the preferred method of testing is to apply a load and thereafter measure the resulting displacement, an alternative test method would be to displace the sample a predetermined distance and then measure the load required to displace the sample the predetermined distance. To provide more control over the material properties, the specimen temperature is held constant by enclosing the shear fixture in an environmental control chamber.

Without limitation, in the preferred embodiment shear tests can be performed to stress levels of 1200 KPA (with 700 KPA supply pressure) and strains to 12% at frequencies from 0 to 10 Hz. The device can perform various tests including a frequency sweep, simple shear and repeated shear to obtain relevant data corresponding to each test, the data of which is required in the superpave modeling technique. The applied load, specimen dimensions, and measured displacement are then analyzed to determine the material stress/strain of the specimen associated with the required test data properties. These properties, along with the controlled temperature, may then be used in the superpave modeling technique to thereby estimate the material's long-term performance.

Further, both dynamic (sinusoidal or pulsed) or static loading can be applied to the shear fixture. A servo pneumatic shear load actuator having a shaft coupled to the shear fixture is used to create the applied load. A servo valve, mounted near the shear load actuator, ports high-pressure supply air (typically 80–175 psi) to either side of an actuator piston. The resulting imbalance of air pressure creates the desired load or force in the desired direction. To energize the servo shear actuator separately from the air supply, an on/off solenoid valve is provided. Those skilled in the art will appreciate that although a servo pneumatic actuator is used to generate the loading, other known load generators could be used including, for example without limitation, a servo hydraulic, electrodynamic or electromechanical actuator.

An environmental control chamber surrounding the shear fixture may be a box type configuration with a door for sealably enclosing the fixture and specimen. The chamber preferably has both hot and cold capability and features an electric heater assembly and liquid $CO_2/N_2$ injector for cooling. Those skilled in the art will appreciate that while a chamber enclosure is used, other heating and cooling means including heating and cooling the material retaining clamps directly could be used. The chamber may include a temperature sensor for temperature readout and control. A signal corresponding to the resulting temperature is transmitted to the microprocessor-based temperature controller for monitoring and control purposes and can be used to ensure that the test is being run at a specific temperature. In this manner, a shear tester is provided that may be used for testing asphalt specimens, for example, at the field site for the purpose of generating test data that can be used in the superpave modeling technique.

These and other advantages of the present invention will become readily apparent to those skilled in the art from a review of the following detailed description of the preferred embodiment especially when considered in conjunction with the claims and accompanying drawings in which like numerals in the several views refer to corresponding parts.

DETAILED DESCRIPTION

Figure 1:
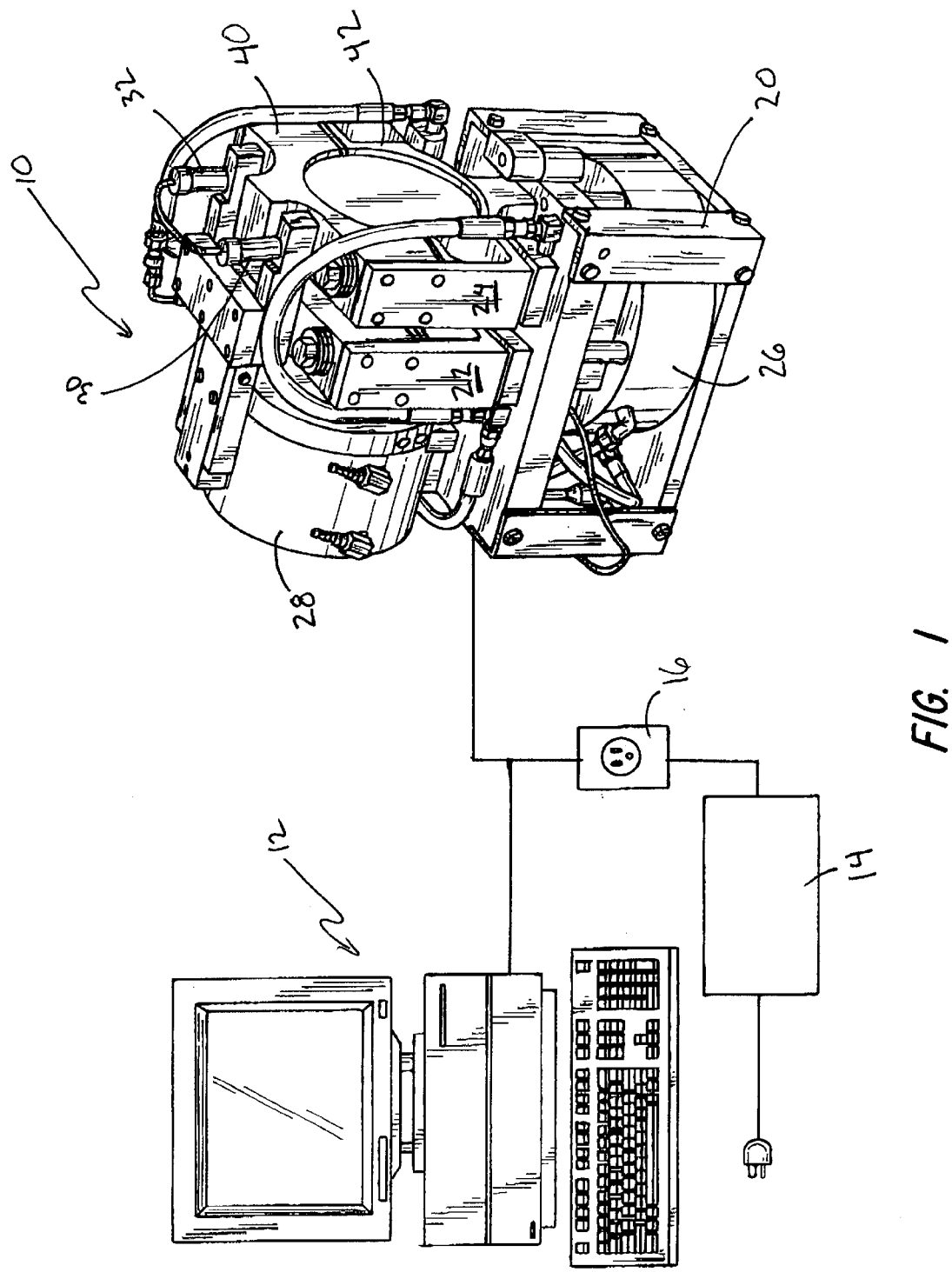
FIG. 1 is a partial perspective fragmentary and block diagram view showing the field shear tester of the present invention removed from the environmental control chamber but coupled to a microprocessor-based control system and power supply.

In conjunction with the several views of the Figures, details of representative embodiments of the present invention will next be presented. Referring first to FIG. 1, there is shown generally the portable shear tester 10 of the present invention electrically coupled to a microprocessor-based controller 12, and an uninterruptible power supply 14 of known suitable construction. To provide a quick shut off capability, a quick stop switch 16 of suitable construction is electrically coupled to the portable shear tester 10 (see also FIG. 3).

The microprocessor-based controller 12 has both RAM (random access memory), and ROM (read only memory) for storing programs and data, which allows for: determining the shear strength of the material specimen, controlling monotonic or dynamic forces applied to the specimen by controlling activation of the shear tester, controlling the activation and sequence of testing by the shear tester 10, and predicting characteristics of the material specimen. The various modes of the controller 12 will be described below in greater detail. While the controller 12 may control the shear tester 10 as described below, those skilled in materials testing will appreciate that other modes may be utilized to measure or test the strength of the material specimen. The field tester 10 may be enclosed within a temperature-controlled chamber 18 (see FIGS. 2 and 3). The microprocessor-based controller 12 may further be utilized to monitor and control the temperature within the chamber 18. The control of the temperature within the chamber 18 will be described below in greater detail.

The Figures including FIG. 1 show the shear tester 10 as generally including a base 20, first and second clamps 22 and 24, actuators 26 and 28, and displacement transducers 30 and 32. A front restraint plate 34 (shown in FIG. 2) is attached to the side of the second clamp 24 with quick release bolts 36 of known suitable construction. In the preferred embodiment, the first and second clamps 22 and 24 each include an upper and lower half or upper and lower restraining member 40 and 42 respectively.

Figure 2:
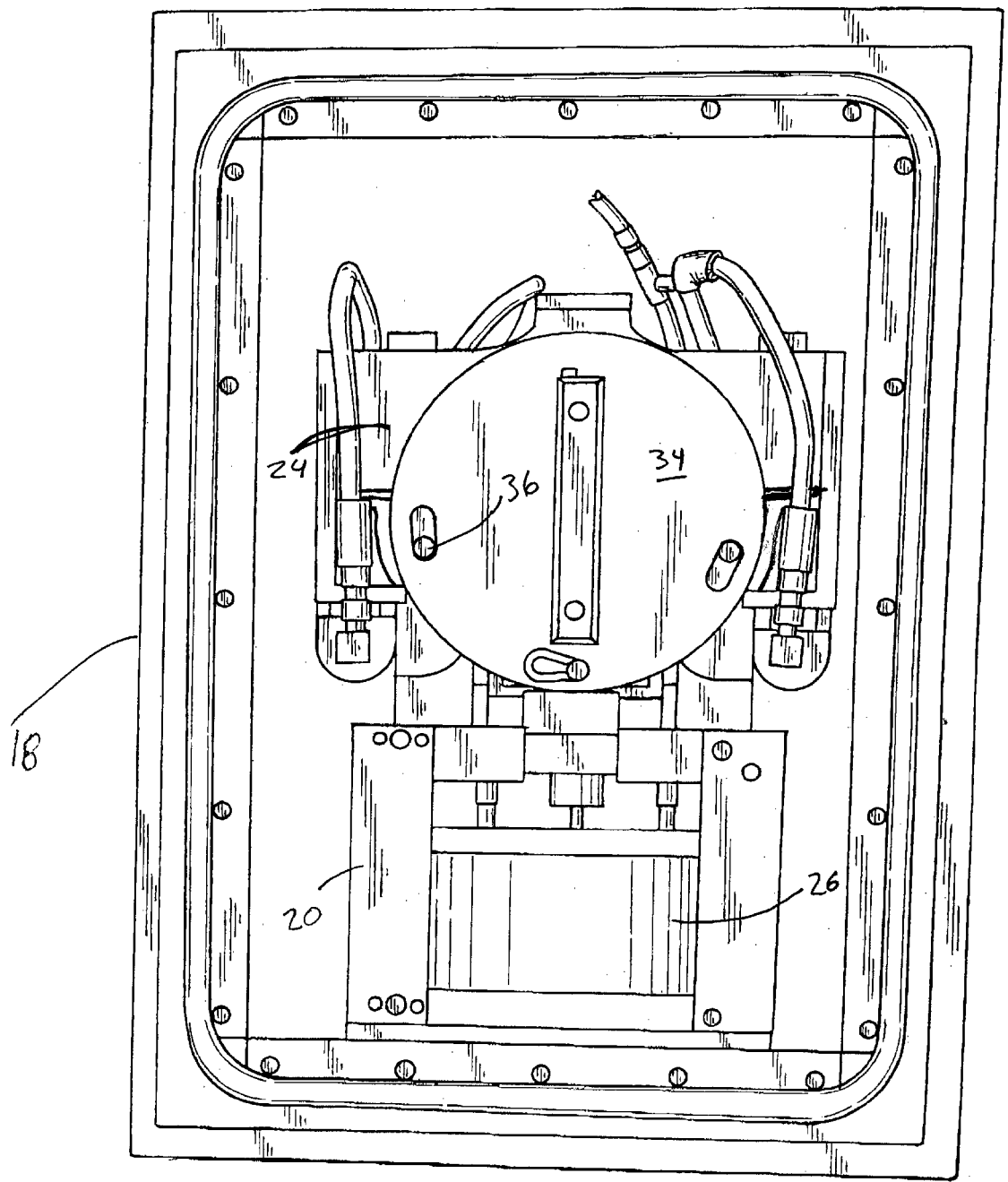
FIG. 2 is a fragmentary front elevational view of the shear tester of the type shown in FIG. 1 and enclosed in an environmental chamber.
Figure 3:
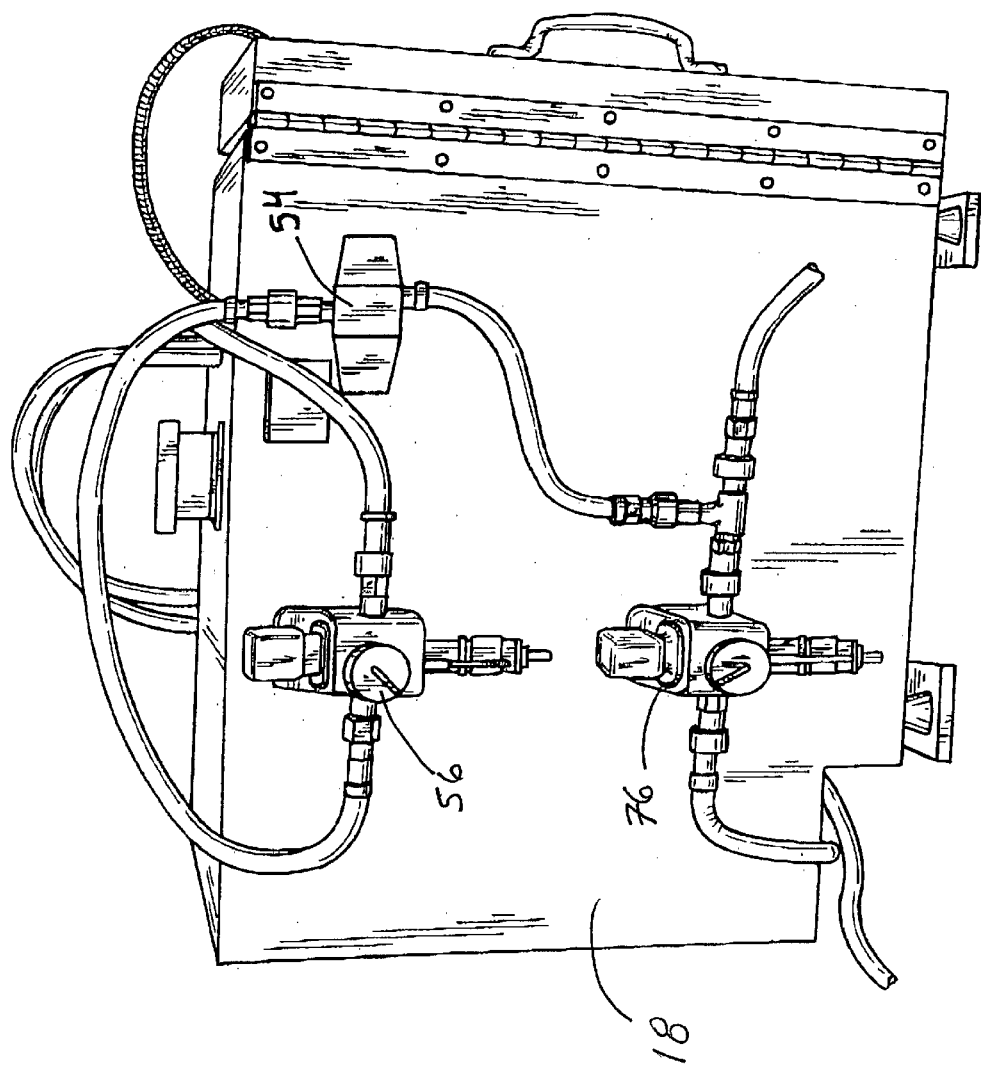
FIG. 3 is a fragmentary side elevational view of the environmental chamber of the type shown in FIG. 2 used to enclose the shear tester.

FIGS. 2 and 3 show the shear fixture 10 contained within the environmental control chamber 18. In order to reduce the influence of temperature variances on the resulting test data, the shear fixture 10 is placed within an environmental control chamber 18, which surrounds the fixture 10. The environmental chamber 18 has hot/cold capability to maintain the temperature at a fixed level throughout the test. The environmental chamber 18 maintains the specimen temperature at a predetermined setting and is capable of either increasing or decreasing the temperature within the chamber 18. In this regard, the chamber has a temperature transducer, an electric heater assembly for heating and a liquid $CO_2/N_2$ injector for cooling.

The temperature transducer and heating/cooling elements within the chamber 18 are coupled to a microprocessor-based temperature controller (not shown) or alternatively temperature control programming may be included in the controller 12 and coupled to the heater and cooler. A signal is sent from the temperature transducer to the temperature controller, indicating the temperature of the chamber air temperature. The microprocessor-based temperature controller uses a PID control algorithm, whereby the temperature transducer signal is compared to a desired setpoint value. The difference or "error" is then scaled using a proportional (P) calculation, integrated over time and scaled using an Integration (I) calculation and differentiated with respect to time and scaled using a Differentiation (D) calculation. The temperature P, I, and D values are then summed together and the resulting value is used to drive a solid-state relay using a Pulse Width Modulation (PWM) technique. When the temperature controller determines that the inside air temperature is below a preset level, the heating elements are activated until the inside air temperature rises to the desired temperature. When the temperature controller determines that the inside air temperature is above a preset level, a solenoid valve is opened thereby cycling $CO_2/N_2$ until the air temperature drops to the desired temperature.

Figure 7:
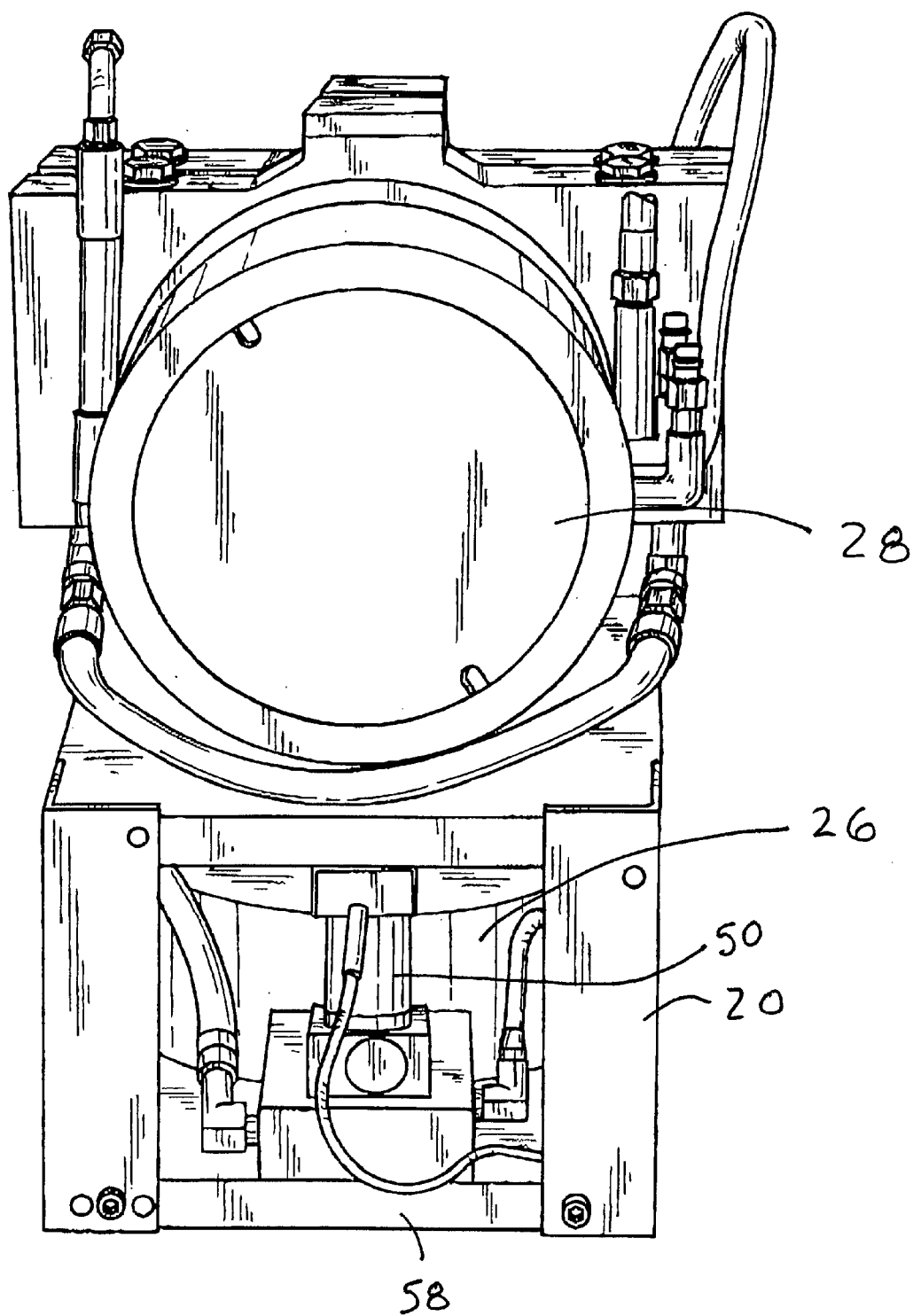
FIG. 7 is a fragmentary back elevational view of the shear tester of the type shown in FIG. 1.

The servo pneumatic actuator 26, of known suitable construction, is attached to the frame 12 (see FIGS. 7 and 9–11) and includes a servo valve 50 (see FIG. 7) for porting air to either side of the shear actuator piston 52. A solenoid valve 54 (see FIG. 3) mounted on the outside of the environmental chamber 18 has on/off capability for manual control of the actuator 26, to thereby isolate the servo valve 50 from the air supply. Maximum applied pressure is set using a pressure regulator 56. In the preferred embodiment, the shear servo actuator 26 is mounted to the bottom baseplate 58 of the frame or base 20 (see FIG. 9). One end of a shaft 60 is attached to the actuator piston 52. The other end of the shaft 60 extends through the actuator endcap 62 and is attached to a universal flexure 64.

Figure 8:
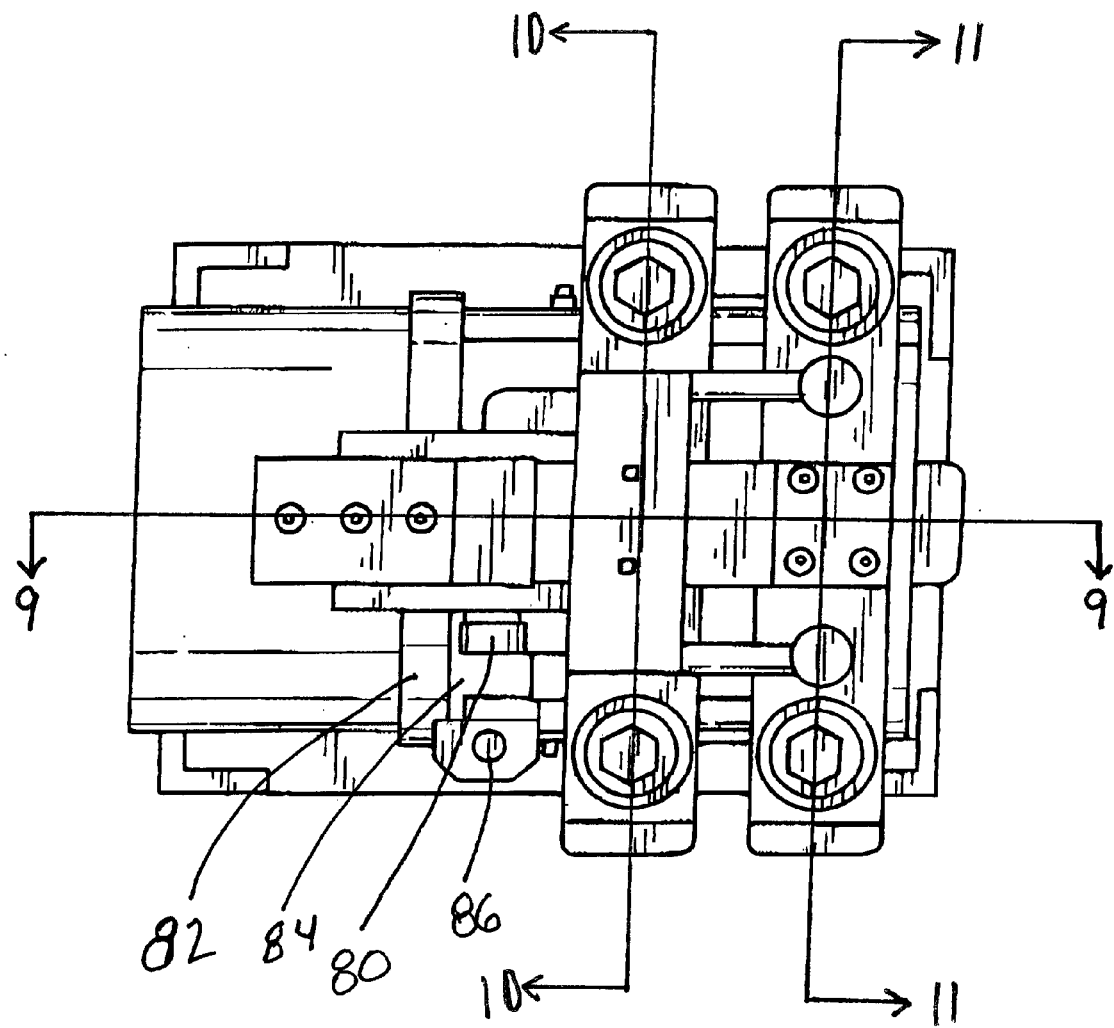
FIG. 8 is a fragmentary top plan view of the shear tester of the type shown in FIG. 1.

Back and front specimen restraints 70 and 34 respectively are used to inhibit the specimen 72 from expanding along its longitudinal axis during testing. The back restraint 70 is attached to a piston 74 of actuator 28. Without limitation, in the preferred embodiment the pneumatic axial load actuator 28 is energized using a hand valve (not shown) and the applied axial load is set using a pressure regulator 76. Additionally, the rear restraint can be locked in place using a clamp block 78 that is preloaded using a hydraulic cylinder 80 (see FIG. 8) of known suitable construction. Without limitation, in the preferred embodiment the hydraulic cylinder 80 has a 1500 pound capacity at 5000 psi. The hydraulic cylinder 80 is mounted to the actuator mount 82 using bracket 84, plumbed through port 86 and actuated via hydraulic hand pump (not shown) mounted to the outside of the environmental chamber 18. The clamp block 78 is mounted directly to the actuator mount 82.

Figure 4:
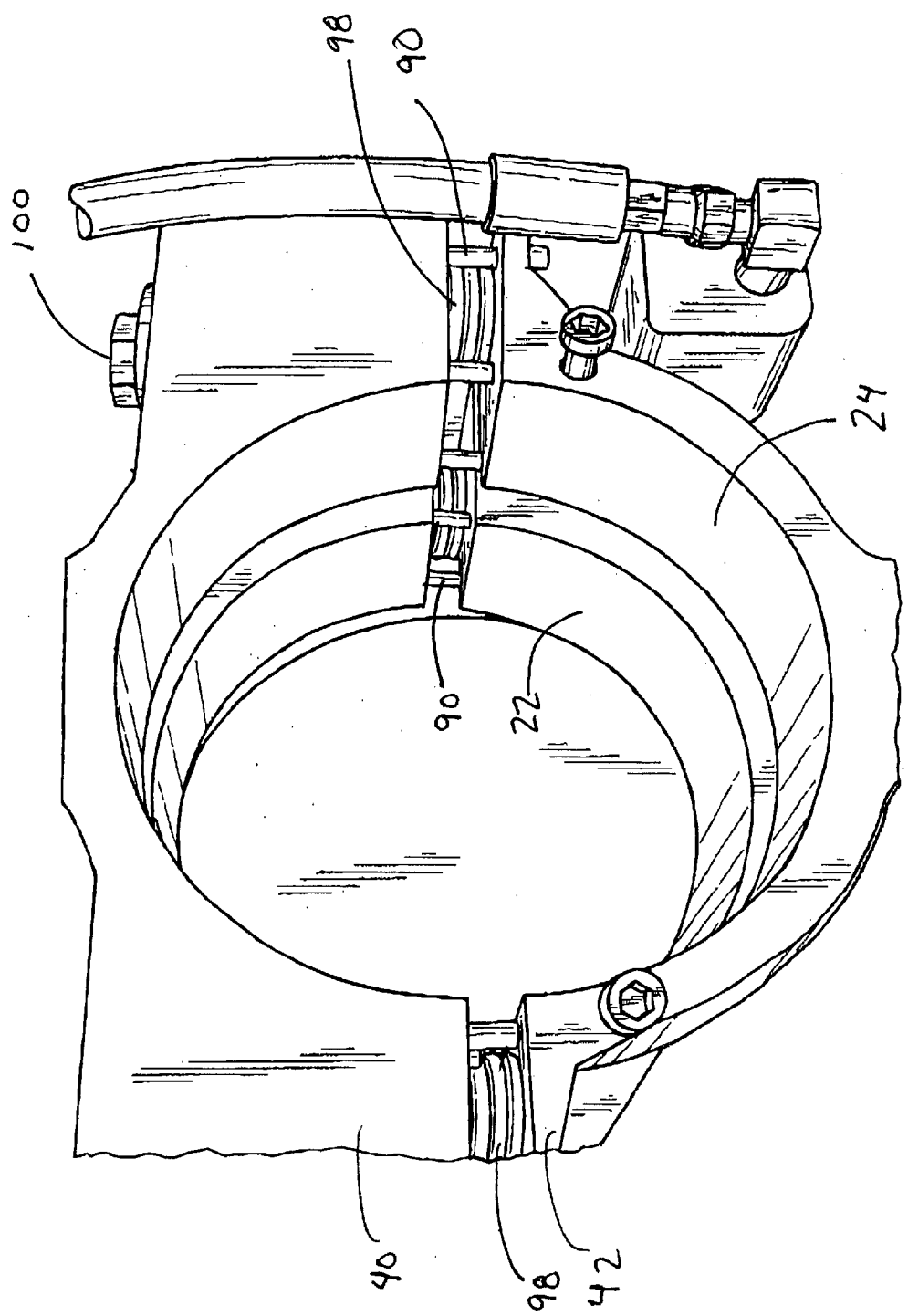
FIG. 4 is a fragmentary front perspective view of the clamps of the shear tester of the present invention.
Figure 5:
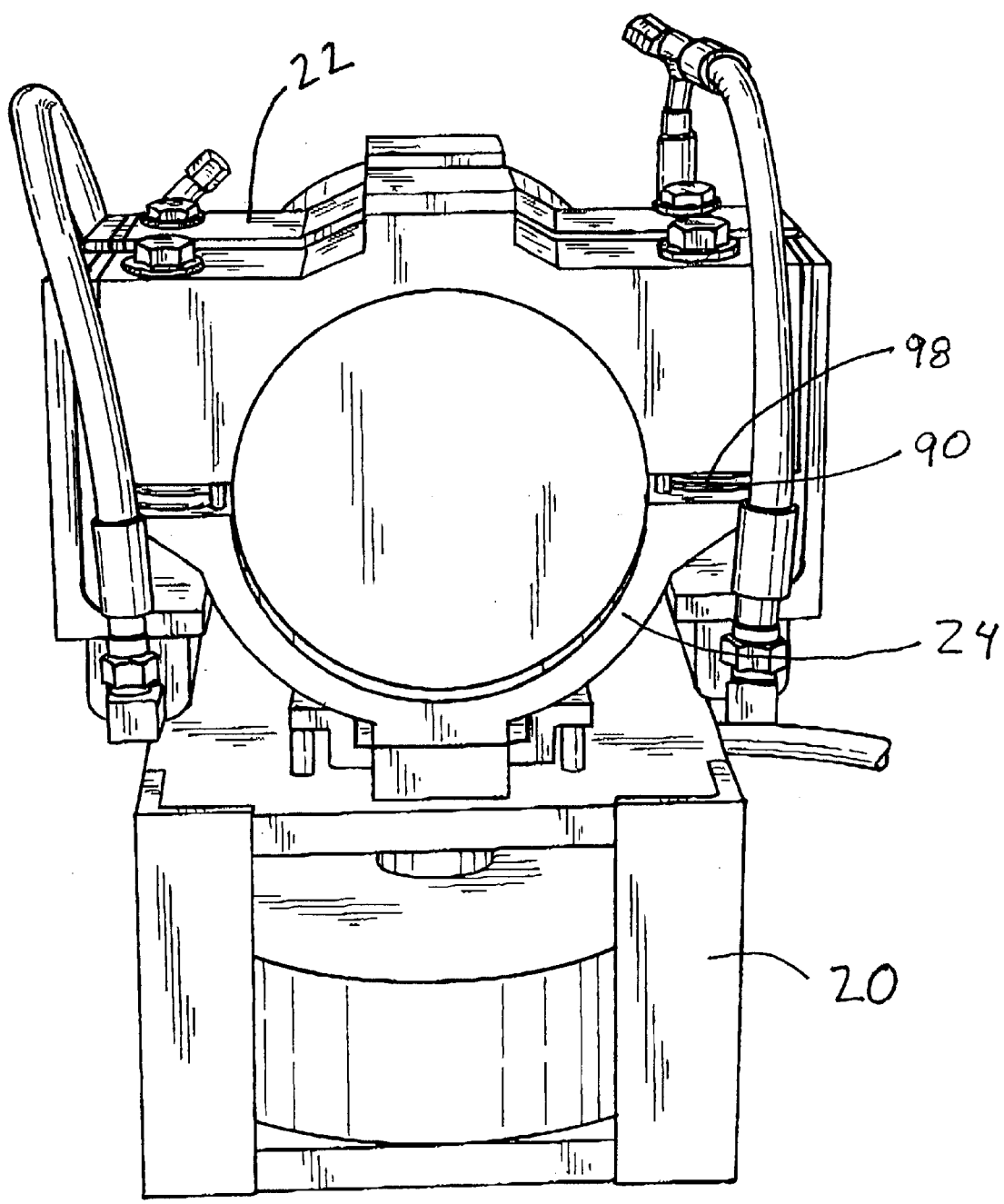
FIG. 5 is a fragmentary front elevational view of the shear tester of the type shown in FIG. 1 with the front plate removed to expose the specimen to view.
Figure 6:
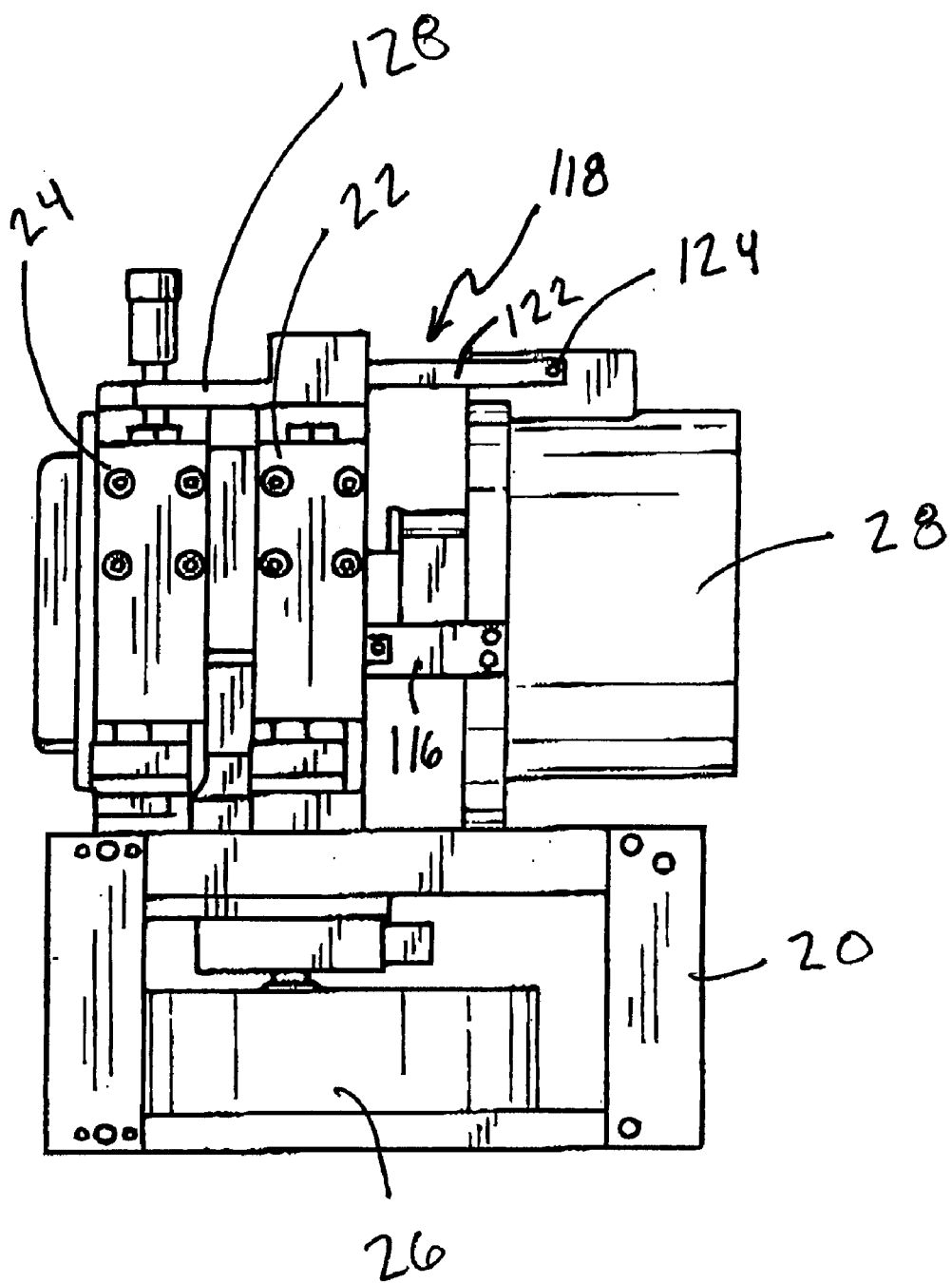
FIG. 6 is a fragmentary side elevational view of the shear tester of the type shown in FIG. 1.

Referring next to FIGS. 4 and 5, the inside surface of the upper and lower restraining members 40 and 42 include concave recesses. The concave recesses are aligned diametrically opposite one another to form a cylindrical pocket to accommodate the material specimen 72, and front and back restraint plates 34 and 70. Alignment of the upper and lower material retaining members 40 and 42 is accomplished using alignment pins 90. The upper and lower material retaining members 40 and 42 are pressed against the specimen using hydraulic cylinders 92 (see FIGS. 10 and 11). The cylinder 92 bodies are mounted to the upper material retaining members 40 using mounting brackets 94. The hydraulic cylinders 92 are plumbed in parallel using ports 96 (see FIG. 11) and actuated by hydraulic hand pump (not shown) mounted external to the environmental chamber 18. When hydraulic pressure is eliminated, complete release of the clamp load applied by the upper and lower material retaining members 40 and 42 is facilitated by coil springs 98. The unlocking spring force is adjusted using adjustment bolts 100.

Figure 9:
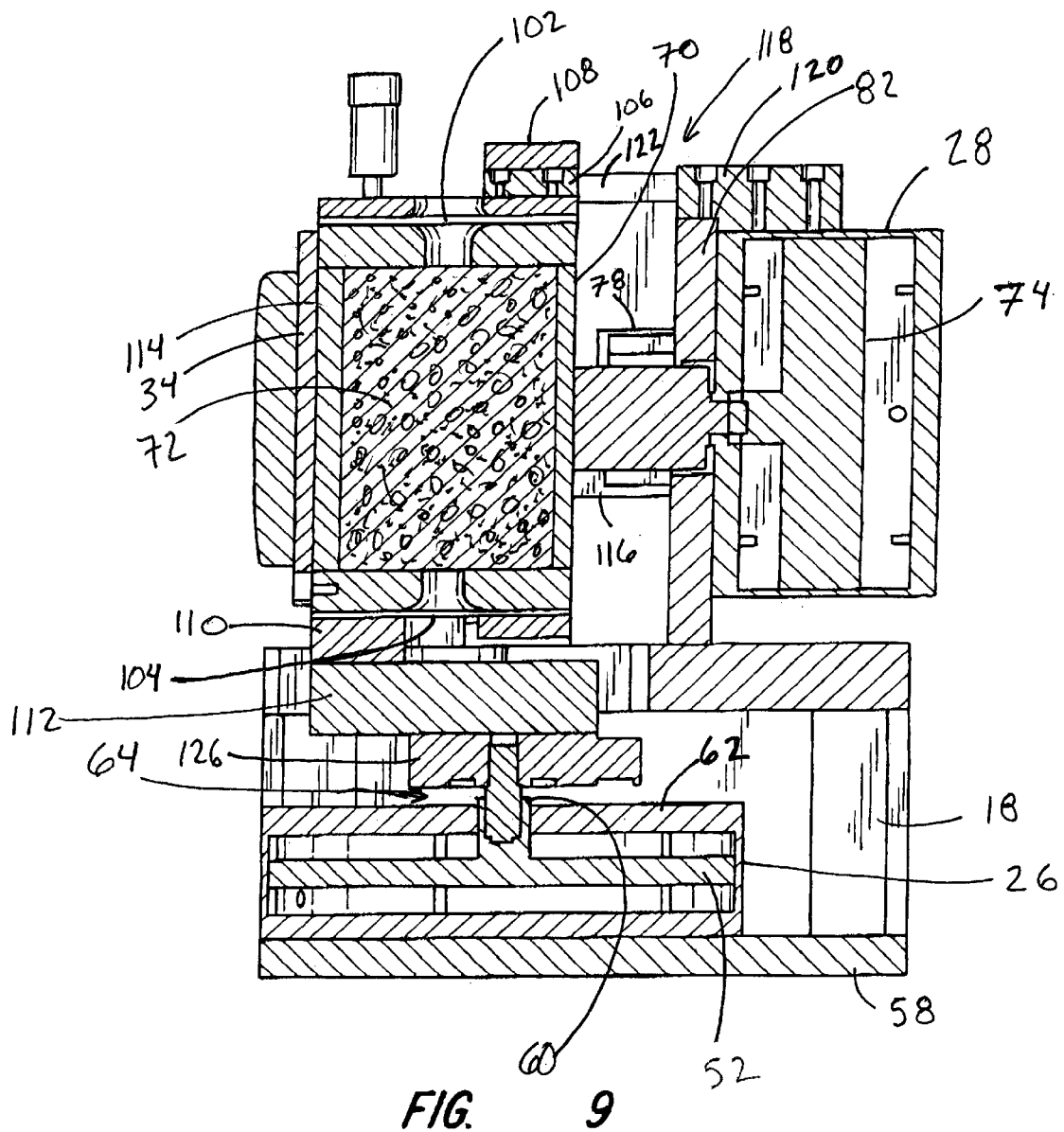
FIG. 9 is a fragmentary partial cross-sectional view taken along line 9—9 of FIG. 8.
Figure 10:
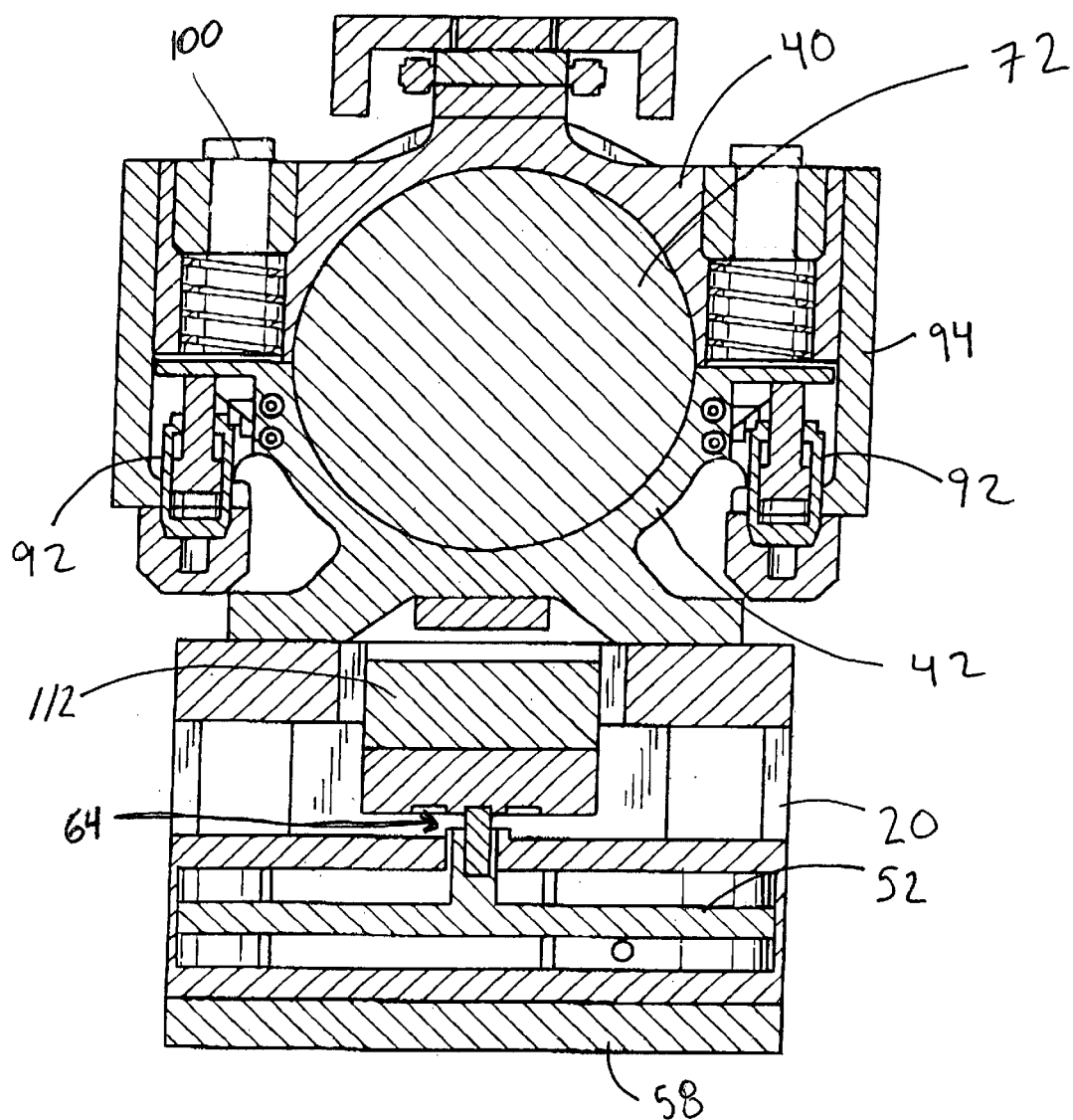
FIG. 10 is a fragmentary partial cross-sectional view taken along line 10—10 of FIG. 8.
Figure 11:
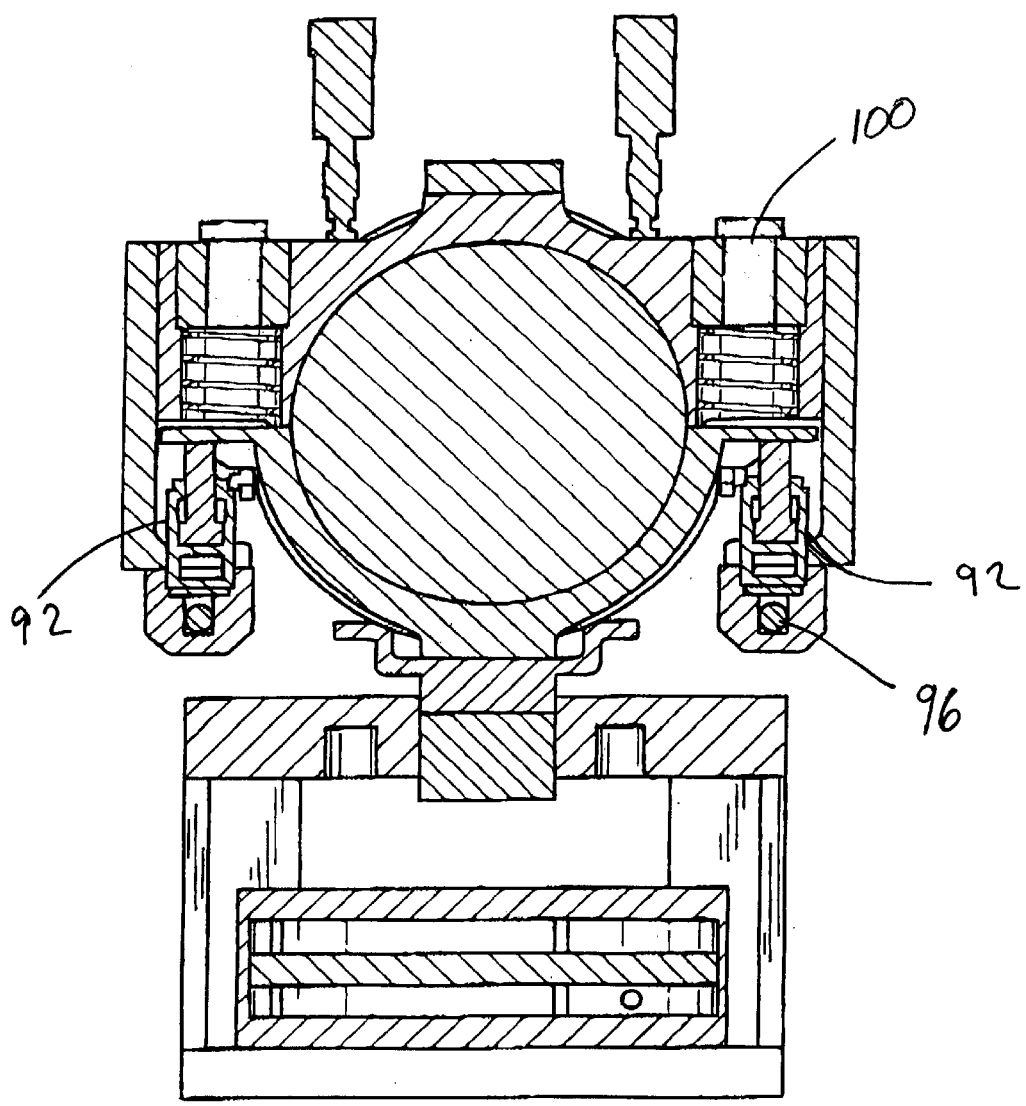
FIG. 11 is a fragmentary partial cross-sectional view taken along line 11—11 of FIG. 8.

Referring now to FIGS. 6 and 8–11 the first and second material retaining clamp assemblies 22 and 24 are attached to upper and lower flexure assemblies 102 and 104 (see FIG. 9). A first end of the upper flexure 102 is attached to the upper retaining member 40 of the first clamp 22. A second end of the upper flexure 102 is attached to the upper material retaining member 40 of the second clamp 24. Likewise, a first end of the lower flexure 104 is attached to the lower retaining member 42 of the first clamp 22; and a second end of the lower flexure 104 is attached to the lower material retaining member 42 of the second clamp 24. The ends of flexures 102 and 104 are clamped to the material retaining members using bolts and clamp blocks 106–110. Clamp block 110 attaches directly to a lower cross-piece 112. The upper and lower flexures 102 and 104 allow movement of the second material retaining clamp assembly 24 in the vertical direction creating a shear condition perpendicular to the specimen's longitudinal axis, while at the same time the flexures 102 and 104 maintain the specimen in fixed position between the material retaining clamp assemblies 22 and 24.

Referring again to FIGS. 2 and 9, the front restraint plate 34 is held in place on the front face of the lower retaining member 42 of the second clamp assembly 24 via shoulder bolts 36. The plate is designed to be easily removed for installation of the cylindrical specimen 72 within the fixture 10. The thickness and spacing of the material clamp assemblies 22 and 24 are constant while and the length of the specimen 72 may vary from 50 to 150 mm, for example without limitation. To accommodate the varied specimen lengths, specimen spacer plates 114 are provided for shorter specimen lengths. The spacer lengths can be fabricated in different thicknesses as needed to accommodate any specimen length.

To prevent an axial load applied to the back specimen restraint plate 70 from creating an overturning moment in the first and second clamp assemblies 22 and 24, brackets and a linkage assembly are used. Brackets 116 attach between the axial actuator mount 82 and the lower retaining member 42 of the first clamp 22 (see FIG. 6). The linkage 118 attached between the actuator body 28 and the upper retaining member 40 of the first clamp 22 and includes the actuator block 120, rear clamp assembly upper clamp block 106, links 122, and link pins 124.

The back plate 70 for the specimen 72 may be utilized for a dual purpose. First, during testing it is used to apply either a constant axial stress or constant axial strain to the specimen. Then, after testing it is used to push the specimen 72 partially out of the fixture 10 so that it can be removed by hand.

As described above the lower retaining member 42 of the second material retaining clamp assembly 24 is attached to the lower cross-piece 112. The lower cross piece is also attached to a load transducer and actuator piston 52. The lower retaining member 42 of the first material retaining clamp assembly 22 is rigidly attached through the reaction framework to the servo actuator body 26. In the preferred embodiment and without limitation, to reduce excessive over travel and damage to the flexure assemblies in the event of a specimen failure, the actuator stroke is limited to ¼" or travel. The short actuator stroke ensures that the material retaining clamp assemblies 22 and 24 can only move a small distance with respect to one another. Universal flexure 64 also reduces extraneous side loads and moments from being transmitted to the load transducer 126 and actuator piston 52.

The applied load or force to the fixture 10 is measured by load transducer 126 that has one end coupled to the lower half of the second clamp assembly 24 by means of a lower crosspiece 112. The other end of the load cell 126 is coupled to universal flexure 64 that is in turn attached to the shaft of the shear load actuator 26. The universal flexure accommodates small angular misalignments while transmitting the applied load to the shear fixture. The body or outer cylinder of the shear load actuator 26 is attached to the load reaction structure. The lower half 42 of the first material retaining clamp assembly 22 is attached directly to the load reaction structure. A signal corresponding to the applied load is transmitted to the microprocessor-based controller 12 which is coupled to the transducer for monitoring and control purposes and can be used to ensure that the test is being run at a specific load amplitude. Those skilled in the art will appreciate that although a load transducer is preferred, one could measure the applied cylinder pressure or motor current in the case where a linear motor is used as the actuation system.

Displacement transducers 30 and 32 are coupled to shear fixture 10. The transducers 30 and 32 are of suitable known construction for measuring the respective displacement of the front material retaining clamp assembly 24 with respect to the rear material retaining clamp assembly 22. The displacement transducers 30 and 32 are electrically coupled to the microprocessor-based controller 12 to provide displacement feedback for closed loop servo control and monitoring. Those skilled in the art will appreciate that although a spring loaded LVDT type displacement transducer is preferred, other transducers used to measure the relative displacement of the first and second material retaining members could be used.

As an upward or downward force is applied by the actuator 26, the load transducer 126 may compress or stretch and the framework will deflect slightly. For this reason, an actuator displacement transducer cannot be used as a reliable indication of relative displacement between the material retaining clamp assemblies 22 and 24. The material retaining clamp assemblies 22 and 24 relative displacement is measured via the two spring loaded displacement transducers 30 and 32 which have their bodies mounted to the upper material retaining member 40 affixed to clamp assembly 22 via bracket 128 (see FIG. 6) and the measuring ends of the transducers 30 and 32 are pressed against the upper material retaining member 40 of clamp assembly 24. Signals corresponding to the measured displacements are transmitted to the microprocessor-based controller 12 for monitoring and control purposes and can be used to ensure that the test is being run at a specific displacement amplitude.

The microprocessor-based controller 12 uses a PID control algorithm for controlling the servo pneumatic actuator 26. The feedback signals from either the load transducer 126 or linear displacement transducers 30 and 32 are amplified and then converted to a digital value by means of an internal analog to digital converter. Over time the resulting digitized feedback value can be represented as a waveform. This waveform is then subtracted from a baseline or desired "command waveform". The resulting waveform or "error signal" is typically sinusoidal with respect to time if the "command waveform" is sinusoidal. Although the control of the servo pneumatic actuator feedback signal may correspond to a load or pressure within the actuator, load control is presently preferred, wherein the displacement feedback is used to monitor the specimen response.

After the error signal is computed, the microprocessor 12 then performs several mathematical operations on the error signal known as PID control. First, the error signal is multiplied by a scaler value K1 to obtain a proportional (P) value. The error signal is also integrated over time and multiplied by scaler value K2 to obtain an Integration (I) value. The error value is also differentiated with respect to time and multiplied by scaler value K3 to obtain a differentiation (D) value. The P, I, and D values are then summed together and converted to a proportional drive output voltage by means of a digital to analog converter built into the microprocessor-based controller 12. This output voltage is the input signal for the servo valve 50, which controls the force applied by the actuator. The PID control tends to reposition the applied load of the servo pneumatic actuator 26 to minimize the error signal.

To further enhance the accuracy of the control loop and maintain the desired applied load, the peak end levels of the feedback signal from load transducer 126 is monitored by the microprocessor based controller 12. If the peak end levels of the feedback signal vary from a predetermined peak level (i.e.: due to changing specimen compliance conditions, changes in supply pressure, etc.), the software automatically adjusts the command waveform used in the PID control until the desired feedback signal end level is achieved.

Having described the constructional features of the present invention, the mode of use will now be discussed. In order to load a specimen 72 into the fixture 10, the user retracts the back plate 70. The user then removes the front plate 34 from the lower material retaining member 42 of the second clamp assembly 24, by turning the front plate 34 slightly counter clockwise until the larger diameter holes fit over the shoulder bolts 36. The user then removes any clamp pressure on the material retaining clamp assemblies 22 and 24 by releasing any pressure applied by the hydraulic pumps. After inserting the specimen 72 until it is flush against back restraint plate 70, the user inserts any required spacer plates and then reattaches the front specimen restraint plate 34 by placing it over the shoulder bolts 36 and rotating it slightly. The operator then loads the back plate against the specimen 72 by applying a pneumatic pressure to the axial actuator. The operator then engages the clamps 22 and 24 against the specimen 72 by activating the corresponding hydraulics. Once the specimen 72 is clamped within the fixture 10, the user can optionally lock the back restraint plate 70 in place using the corresponding hydraulics. With the specimen installed, the user selects the desired applied load profile using the microprocessor-based controller. As the desired load (frequency sweep, simple shear, and repeated shear) is applied, the microprocessor based controller 12 measures the applied load and resulting displacement as a function of time. Depending on the material characteristic to be determined, the microprocessor program performs the required analysis and data storage. Upon completion of the test, the user removes the applied clamp pressure using the release valve on the hydraulic pump, optionally unlocks the back specimen restraint locking mechanism, retracts the back specimen restraint plate 70, removes the front specimen restraint plate 34, extends the back specimen restraint plate 70, and extracts the specimen 72 from the shear fixture 10.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A system for testing a response of a generally cylindrical material specimen, characterized by two ends, a length and a periphery to transverse shear forces applied across the cylindrical material specimen, said system comprising:
   (a) a base;
   (b) a stationary holding device attached to said base for clamping about the periphery of said cylindrical material specimen near one end thereof, wherein said stationary holding device further comprises a pair of aligned opposed retaining clamp members, each having a concave arcuate surface, disposed to provide circumferential clamping of the specimen;
   (c) a movable holding device for clamping about the periphery of said cylindrical specimen near another end thereof, wherein said movable holding device comprises a pair of aligned opposed retaining clamp members, each having a concave arcuate surface, disposed to provide circumferential holding of the specimen;
   (d) flexure members each having two ends, one of which is connected to each of said holding devices in a manner such that a force applied to said movable holding device in a direction transverse of a longitudinal axis of said specimen applies a corresponding transverse shear force to said specimen in relation to the relative displacement of said holding devices and the corresponding connected ends of said flexure members; and
   (e) an actuator attached to said movable holding device wherein said actuator applies a force to said movable holding device which thereby applies said transverse shear force against said specimen.

2. A system as in claim 1 wherein each said pair of aligned opposed retaining clamp members are held in compressive relation to said specimen using a fluid-operated device.

3. A system as in claim 2 further comprising an actuator coupled to said stationary holding device wherein said actuator applies a compressive force against an end of said specimen.

4. A system as in claim 3 further comprising linear displacement transducers coupled to said movable holding device to thereby measure the relative displacement between said stationary and said movable holding devices when the circumferential transverse shear force is applied to the specimen.

5. A system as in claim 1 further comprising an actuator coupled to said stationary holding device wherein said actuator applies a compressive force against an end of said specimen.

6. A system as in claim 5 further comprising linear displacement transducers coupled to said movable holding device to thereby measure the relative displacement between said stationary and said movable holding devices when the circumferential transverse shear force is applied to the specimen.

7. A system as in claim 6 further comprising a control device for adjusting the force applied by said actuator to said movable holding means and for selectively monitoring or controlling said relative displacement between said holding devices.

8. A system as in claim 5 further comprising a control device for adjusting the force applied by said actuator to said movable holding means and for selectively monitoring said relative displacement between said holding devices.

9. A system as in claim 1 further comprising linear displacement transducers coupled to said movable holding device to thereby measure the relative displacement between said stationary and said movable holding devices when the circumferential transverse shear force is applied to the specimen.

10. A system as in claim 9 further comprising a control device for adjusting the force applied by said actuator to said movable holding means and for selectively monitoring or controlling said relative displacement between said holding devices.

11. A system as in claim 1 further including a temperature control system for controlling a temperature of the specimen.

12. A system as in claim 11 further comprising a control device for adjusting the force applied by said actuator to said movable holding means and for selectively monitoring or controlling said relative displacement between said holding devices.

13. A system as in claim 1 further comprising a control device for adjusting the force applied by said actuator to said movable holding means and for selectively monitoring or controlling said relative displacement between said holding devices.

14. A system as in claim 13 wherein said control device is programmable.

15. A system as in claim 14 wherein said control device is microprocessor-based.

* * * * *